US008607641B2

(12) United States Patent
Lilley et al.

(10) Patent No.: US 8,607,641 B2
(45) Date of Patent: *Dec. 17, 2013

(54) CLAMPING MECHANISM FOR SHEAR TESTING APPARATUS

(71) Applicant: Nordson Corporation, Westlake, OH (US)

(72) Inventors: David Lilley, Colchester (GB); Martin Bugg, Ipswich (GB); Robert John Sykes, Essex (GB)

(73) Assignee: Nordson Corporation, Westlake, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/850,460

(22) Filed: Mar. 26, 2013

(65) Prior Publication Data

US 2013/0186207 A1 Jul. 25, 2013

Related U.S. Application Data

(63) Continuation of application No. 13/035,217, filed on Feb. 25, 2011, now Pat. No. 8,424,390.

(30) Foreign Application Priority Data

Mar. 5, 2010 (EP) ..................................... 10002332

(51) Int. Cl.
*G01N 3/24* (2006.01)
(52) U.S. Cl.
USPC .............................................. 73/841; 73/842
(58) Field of Classification Search
USPC ............. 73/827, 841, 842; 279/145; 356/244
See application file for complete search history.

(56) References Cited

U.S. PATENT DOCUMENTS

| 5,144,845 | A | 9/1992 | Pyke |
| 5,685,193 | A | 11/1997 | Hurtubise et al. |
| 6,078,387 | A | 6/2000 | Sykes |
| 6,301,971 | B1 | 10/2001 | Sykes |
| 8,424,390 | B2 * | 4/2013 | Lilley et al. ..................... 73/841 |
| 2004/0103726 | A1 | 6/2004 | Cox |
| 2008/0190212 | A1 | 8/2008 | Sykes |
| 2008/0257059 | A1 | 10/2008 | Peecock et al. |

FOREIGN PATENT DOCUMENTS

WO    2007093799 A1    8/2007

OTHER PUBLICATIONS

European Patent Office, European Search Report in EP Application No. 10002332, Jul. 29, 2010.

* cited by examiner

*Primary Examiner* — Leonard Chang
*Assistant Examiner* — Irving A Campbell
(74) *Attorney, Agent, or Firm* — Wood, Herron & Evans, L.L.P.

(57) ABSTRACT

A shear test device for testing the strength of attachment between a bond and an electronic substrate. The device incorporates a clamping mechanism and a shear test tool that are mounted on a baseplate. During a set-up procedure, the shear test tool is movable relative to the baseplate. During a test procedure, the shear test tool is clamped by the clamping mechanism in a fixed position relative to the baseplate. At least one abutment is provided that is fixed in position relative to the baseplate. During the test procedure, a drive mechanism provides relative movement between the shear test tool and the bond to cause the shear test tool to shear the bond off the substrate. The at least one abutment provides an additional clamping force on the test tool while the test tool is shearing the bond off of the substrate.

15 Claims, 8 Drawing Sheets

CLAMPING MECHANISM FOR SHEAR TESTING APPARATUS

CROSS-REFERENCE TO RELATED APPLICATION

This application is a continuation of application Ser. No. 13/035,217, filed Feb. 25, 2011 (pending) which claims the priority of European Patent Application No. 10002332.4, filed Mar. 5, 2010 (pending), the disclosures of which are hereby incorporated by reference herein.

FIELD OF THE INVENTION

The present invention relates to shear testing tools. In particular, the invention relates to a device and method that allows movement of a shear testing tool relative to a mounting plate during a set-up procedure but maintains the shear testing tool in a fixed position relative to the mounting plate during a shear test procedure.

BACKGROUND TO THE INVENTION

Semiconductor devices are very small, typically from 5 mm square to 50 mm square, and typically comprise numerous sites for the bonding of electrical conductors to the semiconductor substrate. Each bond consists of a solder or gold ball deposit adhered to the substrate. It is necessary to test the strength of the attachment between the bond and the substrate, known as the bond strength, in order to be confident that the bonding method is adequate and that the bond strength is sufficient. Because of the very small size of the bonds, tools used to test the bond strength must be both very accurately positioned and able to measure very small forces and deflections.

A known test device, as described in WO2007/093799, has a test tool for engagement with a bond. The test tool is used to shear a bond off a semiconductor substrate and the force required to shear the bond is recorded. A force transducer is incorporated into the test tool in order to measure the force.

In order to ensure repeatability, it is essential for the tip of the test tool to engage the side of the bond at a predetermined height above the surface of the substrate. This distance is small but critical, since the bond is usually dome-shaped. A predetermined spacing from the surface eliminates both sliding friction from the test tool on the substrate, and ensures that the shear load is applied at a precise location in relation to the bond interface. Accordingly, in practice, the test tool is first moved into contact with the substrate surface and then withdrawn by a predetermined distance, typically 0.05 mm or less before the shear test is performed.

Several difficulties arise. Friction and stiction in the mechanism of the device itself may cause difficulties in sensing contact with the substrate surface. Imprecise surface sensing will inevitably affect the distance by which the test tool is withdrawn, and thus the height at which the bond is sheared. The distances involved are very small and so care needs to be taken to sense the exact moment of surface contact, without compression of the substrate. Care must also be taken to prevent uncontrolled movement of the test tool at the test height prior to or during the shear test. Such movement may seriously affect the accuracy of the test results and significant movement of the test tool at the test height may damage an adjacent bond or wire.

The twin objectives of both a low contact force when sensing the surface of the substrate and accurate control of the test height are difficult to resolve.

U.S. Pat. No. 6,078,387 discloses a device for sensing contact of a test head of a test tool with the substrate which is adapted to immediately stop downward drive of the test head when contact is sensed. The test tool is supported on the free end of a pair of cantilever arms which are secured at their opposite ends to a baseplate and deflects to allow some vertical movement of the test head with respect to the baseplate. To prevent vertical movement of the test head during the shear tests, test tool is spring biased by the cantilever arms against the baseplate. The test head can be moved away from the baseplate by an air-bearing to allow the test head to move vertically in a substantially frictionless manner for initial contact sensing. Thus, when the test head first touches the substrate surface, it is pushed back by the substrate surface on the cantilever arms. Movement of the test head relative to the baseplate or movement of the cantilever arm can be detected by an optical detector, and the air-bearing is then switched off to ensure that the test head is fixed relative to the baseplate by the spring bias of the cantilever arms against the baseplate. Once the test head is fixed relative to the baseplate, the baseplate is raised by a predetermined amount so as to leave a clearance between the lower end of the test tool and the substrate of the desired "step off distance".

An alternative system is to have the cantilever arms bias the test tool away from the baseplate to allow for substantially friction-free movement of the test head relative to the base plate during initial positioning, but then to press the test tool into contact with the baseplate using a piston driven by compressed air to create a clamping force on the test tool against the baseplate during a test procedure.

Both of these systems are effective for accurately positioning a test head above a substrate whilst providing a relatively low touchdown force in initial positioning of the test tool above the substrate surface. However, they still suffer from some disadvantages.

A first disadvantage is the relatively high cost of these systems. The air-bearing is a relatively expensive component in the overall cost of a shear testing tool.

A second disadvantage is that during a test procedure much of the load has to be supported by the cantilever arms. This means that for tests at higher loads, larger, and consequently more massive, cantilever arms must be used. This in turn leads to a larger touchdown force when initially positioning the sensor, which can lead to damage to the substrate surface. This has also resulted in different cantilever arm assemblies being used for different load tests, further increasing cost.

A third disadvantage is that in both the air-bearing solution and the compressed air activated piston solution, the test head is moved laterally as the cantilever arms are urged or pressed against the baseplate, so that it can be positioned relative to the substrate but prior to the test being performed. The switching off of the air-bearing or the clamping of the test tool against the baseplate inevitably means some vertical movement will occur in addition to the lateral movement of the test head. This movement can reduce the accuracy of the resulting test, especially given the extremely small step off distance involved.

It is therefore an object of the invention to address the abovementioned problems or at least to provide a useful alternative.

SUMMARY OF THE INVENTION

In accordance with a first aspect of the invention, there is provided a shear test device for testing the strength of attachment between a bond and an electronic substrate, such as for testing the bond strength between a solder ball deposit and an electronic substrate, comprising:

an x-y table to which the substrate is attached;

a shear test tool;

a drive mechanism that provides relative movement in a test direction between the table and the test tool;

a baseplate, the shear test tool attached the baseplate by a resilient connector that allows for movement of the shear test tool relative to the baseplate in an axial direction which is perpendicular to the test direction;

at least one abutment rigidly fixed relative to the baseplate, the at least one abutment being in contact with the shear test tool; and a clamping device coupled to the baseplate and moveable between a rest position wherein the device is not forced into contact with the shear test tool and an actuated position wherein the device is forced into contact with the shear test tool to maintain the shear test tool stationary relative to the baseplate in the axial direction, such that when the drive mechanism provides relative movement in the test direction between the x-y table and the shear test tool to cause the shear test tool to shear the bond, or ball deposit, off the substrate during a shear test, the at least one abutment provides an additional clamping force on the shear test tool.

Preferably, the clamping device comprises a single element that contacts the shear test tool in the actuated position. Alternatively, the clamping device may comprise two or more elements that contact the shear test tool in the actuated position.

Preferably, when the clamping device is in the actuated position, the shear test tool is held between the clamping device and the least one abutment.

Preferably, in the actuated position, the clamping device urges the shear test tool into contact with first and second abutments.

Preferably, the clamping device is moveable between the rest position and the actuated position via a pneumatic mechanism.

Preferably, the position of the at least one abutment, and the first and/or second abutments, is adjustable along an axis that is parallel to an axis aligned with the test direction.

Preferably, the resilient connector that allows for movement of the shear test tool relative to the baseplate comprises a pair of cantilever arms.

Preferably, the shear test device further comprises a sensor configured to generate a signal when movement of the shear test tool relative to the baseplate in the axial direction is detected, and a controller connected to the sensor and to the clamping device, wherein the controller is configured to move the clamping device into the actuated position in response to the signal from the sensor.

In a second aspect of the invention, a new method of testing the strength of attachment between a bond and an electronic substrate is described, using a shear test device in accordance with the first aspect of the invention, comprising the steps of:

positioning the test tool a predetermined distance from the substrate in the axial direction;

providing relative movement between the test tool and the bond in the test direction to cause the test tool to shear the bond off the substrate, wherein the force applied by the bond to the test tool causes the at least one abutment in the shear test device to provide a clamping force on the test tool; and recording the force applied to the test tool by the bond.

Preferably, the step of positioning the test tool comprises: moving the test tool in the axial direction towards the substrate; detecting contact between the test tool and the substrate; and stopping the moving of the test tool in the axial direction when contact is detected. Preferably, the method further comprises the step of clamping the test tool to fix the position of the test tool relative to the baseplate following the step of stopping. Preferably, the method further comprises the step of moving the test tool and baseplate away from the substrate a predetermined distance following the step of clamping. Preferably, the method further comprises the step of unclamping the test tool relative to the baseplate following the step of recording.

BRIEF DESCRIPTION OF THE DRAWINGS

Preferred embodiments of the invention will now be described in detail, by way of example only, with reference to the accompanying drawings, in which.

DETAILED DESCRIPTION

Figure 1:
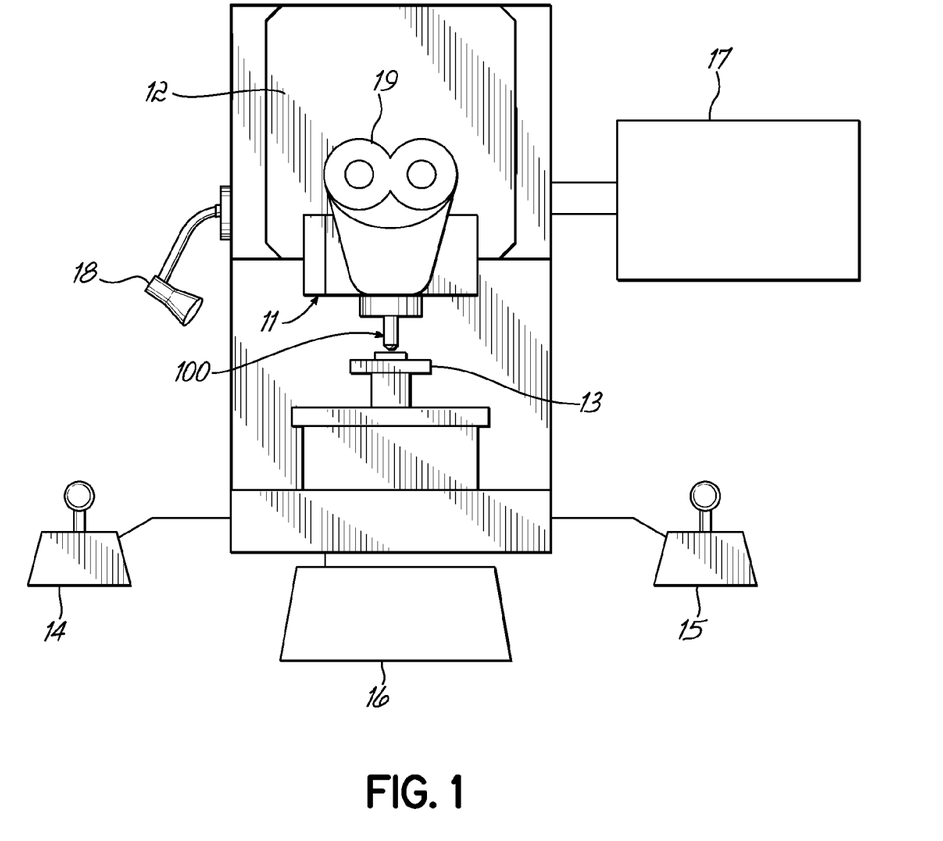
FIG. 1 is a schematic illustration of a shear testing apparatus in accordance with the present invention.
Figure 3:
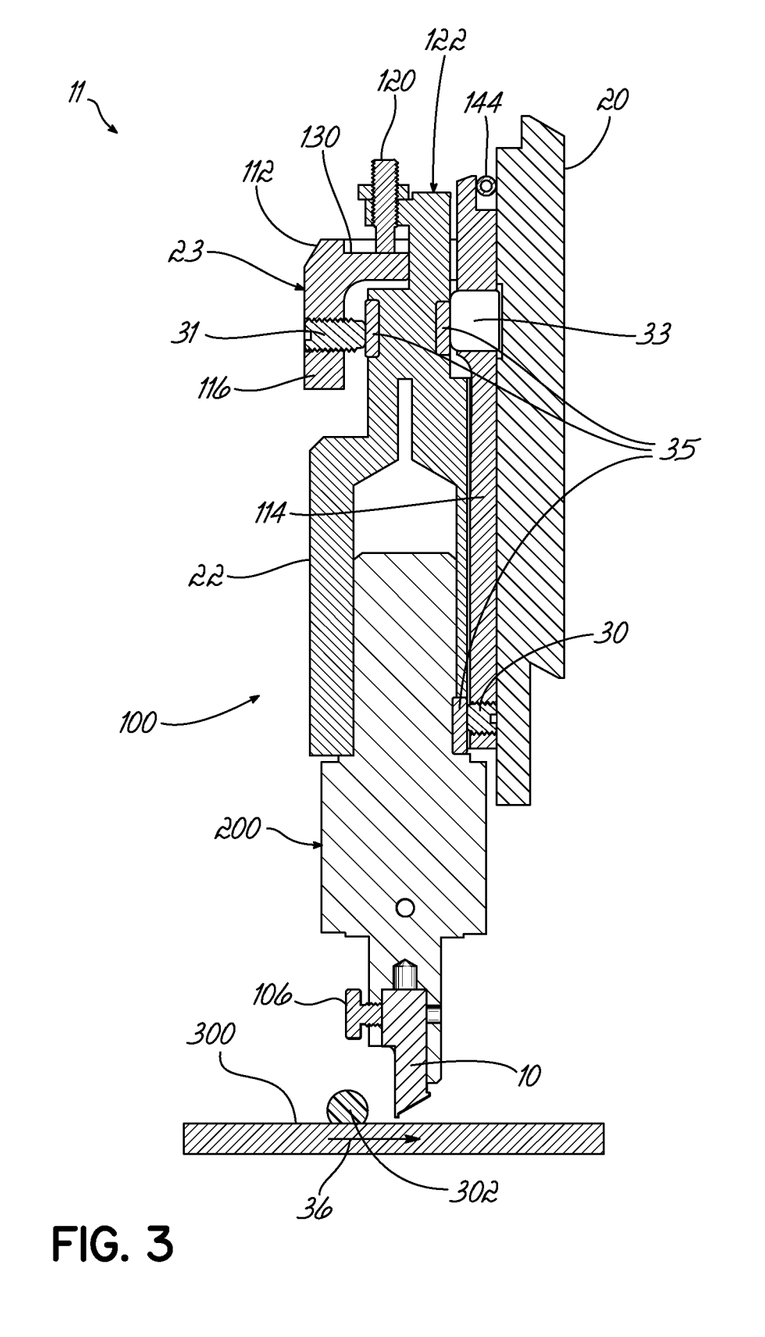
FIG. 3 is a cross-section view of a shear testing device in accordance with the present invention.

FIG. 1 is an illustration of a shear testing device 12 in accordance with the present invention. The device 12 comprises a shear test tool 100 mounted to a cartridge 11, which is itself mounted to the main body of the device 12. Beneath the shear test tool 100 is a motorised stage table 13, on which samples to be tested can be mounted. As shown in FIG. 3, the samples are typically substrates 300 upon which solder ball deposits 302 are formed that are connected to electronic circuitry (not shown) within the substrate 300.

As best shown in FIG. 3, the shear test tool 100 includes a shear test head 10 that is secured in a tool holder 200, which is in turn secured in a shear seam body 22. As will later be described in more detail, the test head 10 applies a shear force to the ball deposits 302 on a substrate 300 under test. The shear test tool 100 includes strain gauges (later described) for measuring the shear force experienced by the test head 10 as the ball deposit 302 is sheared off the substrate 300 under test.

The shear tool 100 is held in a cartridge 11 (in a manner later described) and is moveable in a direction normal to the substrate 300, herein after referred to as the Z-direction or axial direction. Movement of the shear tool 100 in the Z-direction is achieved by movement of the cartridge 11 relative to the main body 12. The cartridge 11 is mounted to the main body 12 by a ball screw, or leadscrew and nut (not shown), and can be driven by an axial drive mechanism such as a servo motor or stepper motor (not shown), or any other suitable, controllable drive arrangement as is well known in the prior art. See, for example, the Dage 4000 Multipurpose Bond Tester available from Dage Holdings Limited, 25 Faraday Road, Rabans Lane Industrial Area, Aylesbury, Buckinghamshire, United Kingdom.

The stage table 13 is movable parallel to the plane of a substrate 300 under test, herein after referred to as the X-Y plane. This allows ball deposits 302 to be moved along a test direction axis in a test direction towards and past the shear test tool 100 during a test procedure. Movement of the stage table 13 is again achieved using suitable servo motors or stepper motors coupled to the table via a leadscrew and nut, ballscrew and nut or suitable belt drive mechanism, as is also well known in prior art such as the Dage 4000 Multipurpose Bond Tester referenced above.

Also shown in FIG. 1 are control devices, comprising two joystick controls 14, 15 for controlling the movement of the stage table 13, and a keyboard 16. A display 17, a light 18 for illuminating the substrate under test, and a microscope 19 aiding accurate positioning of the test tool, are also shown. These features are also all well known in prior art such as the Dage 4000 Multipurpose Bond Tester referenced above.

Figure 2:
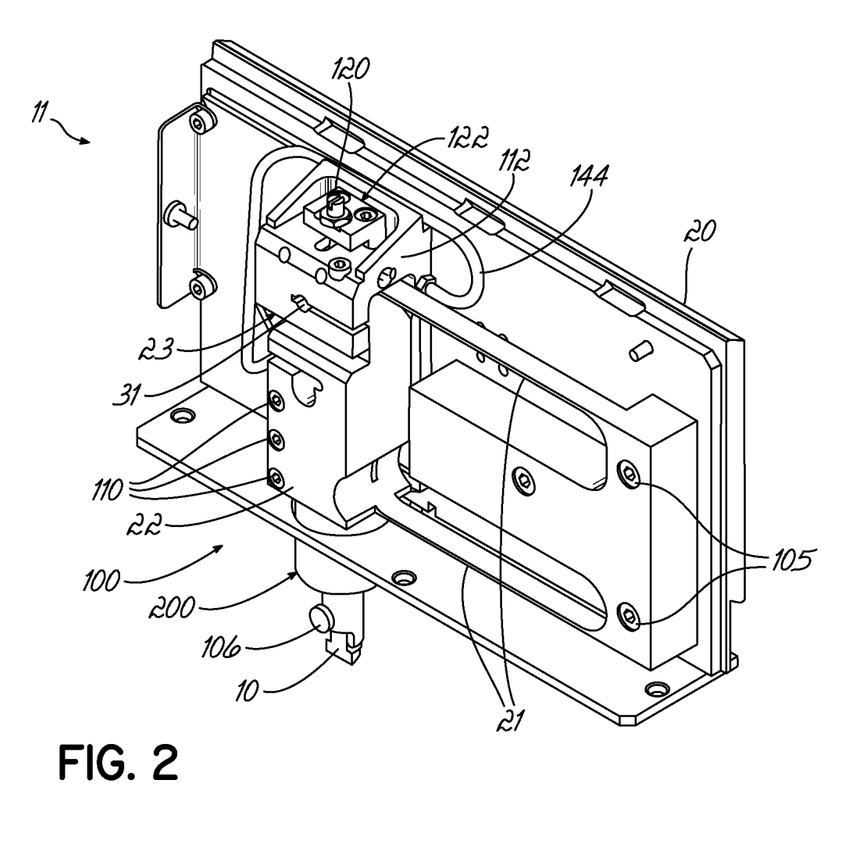
FIG. 2 is a perspective view of a shear testing device, in accordance with a the present invention.
Figure 4:
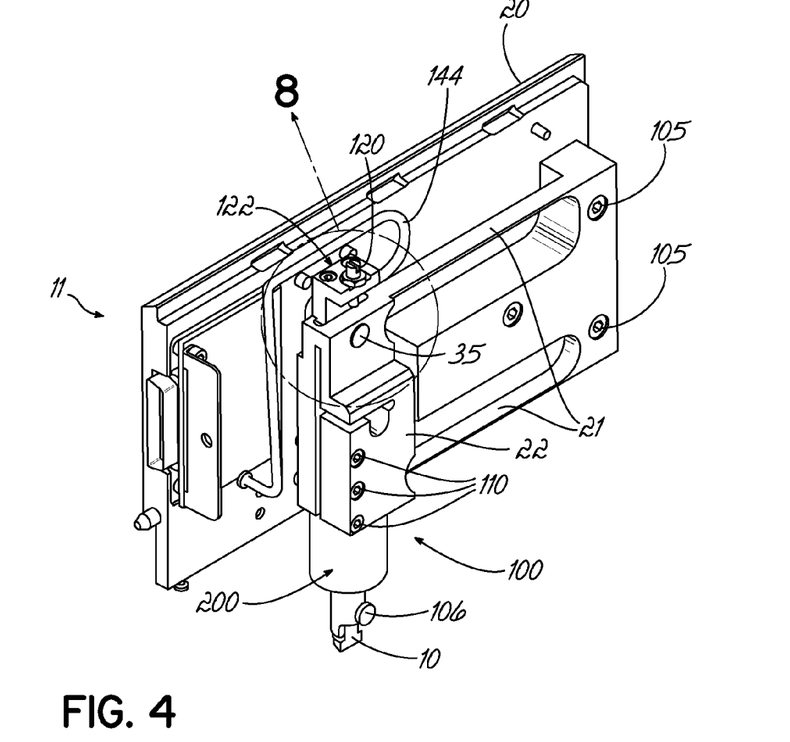
FIG. 4 is another perspective view of the shear testing device of the present invention, with the clamp support block 23 removed.
Figure 5:
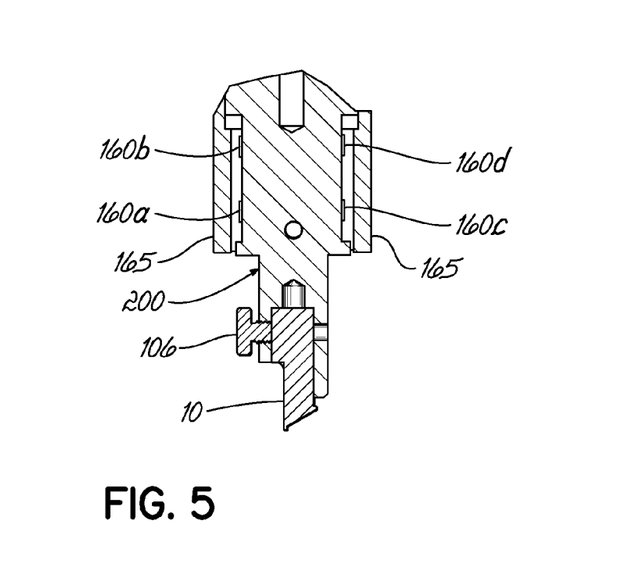
FIG. 5 is a cross sectional view showing the mounting of the shear tool 10 to the tool holder 200, and the strain gauges 160a-160d, in more detail.

With reference to FIG. 2, the cartridge 11 comprises a backplate 20, to which one end a pair of cantilever support arms 21 is rigidly attached using screws 105. The cantilever support arms 21 support shear test tool 100 at their opposite ends. Shear test tool 100, in one preferred embodiment, comprises a shear beam body 22 to which is attached a tool holder 200, to which is attached a test head 10. As best shown in FIG. 4, shear beam body 22 has a split clamp design. Tool holder 200 is inserted into the body 22 and then screws 110 are tightened to clamp holder 200 securely into the body 22. The tool holder 200 is fitted with a dowel pin protruding from the clamped portion of its shaft. The dowel pin is received in the split of the split clamp 22, such that the rotational position of the tool relative to the shear beam body 22 is assured. The shear test head 10 is in turn attached to the tool holder 200 by a thumb screw 106 as best shown in FIG. 5. The test head 10 has a flat on a front surface, onto which the thumb screw 106 operates. Fastening the thumb screw against the flat ensures that the test head 10 is in the correct rotational orientation relative to the tool holder 200. The cantilever arms 21 allow the shear test tool 100, comprised of the shear beam body 22, tool holder 200 and test head 10, to move in the Z-direction with very little friction.

Although the example illustrated in FIG. 2 uses a pair of cantilever arms 21 in order to allow the shear test tool 100 to move in the Z-direction, other resilient mounting arrangements may be used, for example a compression spring.

A clamp support block 23 is rigidly fixed to the backplate 20. The clamp support block 23 has a hood portion 112 that extends around the shear beam body 22, and a backplate portion 114 which is attached to backplate 20 such as by screws (not shown). A portion 116 of the clamp support block 23 is positioned on an opposite side of the shear beam body 22 to the backplate 20. When the clamping mechanism (later described) is not in its actuated position, the shear beam body 22, and therefore the shear test tool 100, is free to move up and down within the clamp support block 23.

Figure 6:
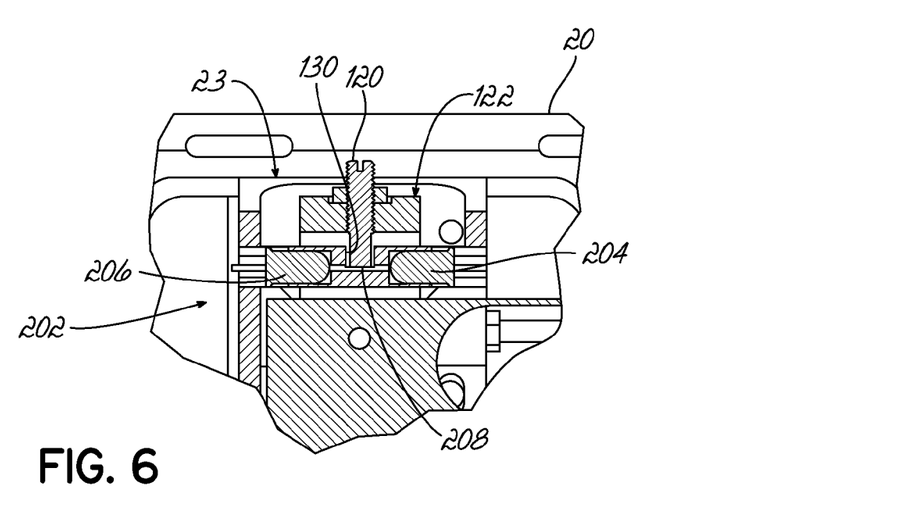
FIG. 6 is a partial cross-sectional view of the elements of the optic sensor 202 and the touchdown adjusting screw 120.

The cartridge 11 includes an optical sensor 202 for detecting when the test head 10 of shear tool 100 contacts the substrate. As best shown in FIG. 6, the sensor 202 is supported in the clamp support block 23. The sensor 202 includes an emitter 204 and a receiver 206. The emitter 204 projects a light beam through aperture 208 formed in the clamp support block 23.

A touchdown adjusting screw 120 is threaded into a touchdown block 122. Touchdown block 122 is attached to shear beam body 22 by screws 124 best shown in FIG. 8. With reference to FIG. 6, touchdown adjusting screw 120 projects through a slot 130 (shown in FIGS. 6 and 7) and can be threaded down into contact with the bottom 132 of slot 130 to block the light beam emitted from emitter 204 and prevent it from being detected by receiver 206.

As this screw 120 is threaded down against the surface 132, it exerts an upward force on the test tool 100, lifting the test tool 100 against the bias of the cantilever arms 21. The greater the distance that the test tool 100 is lifted by screw 120, the greater the force of the cantilever arms that biases the screw 120 against the surface 132 of the clamp support block 23.

When the tool 100 is moved downwardly into contact with the substrate 300, the bottom end of the screw 120 is lifted off of the surface 132 to a position where it no longer blocks the light beam from emitter 204. This causes the receiver 206 to detect the beam and thereby indicate to the control system (later described) that the tool 100 has contacted the substrate 300.

If the screw 120 is only lightly contacting the surface 132, only a light touchdown force is required to lift the end of screw 120 off the surface 132. If, on the other hand, the screw 120 is threaded down to contact the surface 132 with greater force, a greater touchdown force is required to move the end of screw 120 up from contact with surface 132. Therefore, the degree to which screw 120 is threaded down through the touchdown block 122 into contact with surface 132 of the clamp support block 23 determines the amount of touchdown force required to allow the optic sensor 202 to detect contact of the shear test tool 100 with the substrate 300.

The sensor 202 is coupled to touchdown electronics 47 (later described with reference to FIG. 9) that also controls the axial drive mechanism for the cartridge 11 and the shear tool 100, and the movement of the x-y table 13. When movement of the shear tool 100 upward relative to the backplate 20 is detected by detection of the optic beam by receiver 206 as described above, further downward movement of the cartridge 11 relative to the main body 12 by the axial drive mechanism is stopped. At this point, it is necessary to prevent further movement of the test tool 100, so that the test tool 100 can be accurately positioned relative to the substrate 300. The system of the present invention uses a pre-clamp mechanism (later described) to hold the shear test tool 100 in place relative to the cartridge backplate 20, once touchdown of the tool 100 on the substrate has been detected.

As shown in FIG. 3, the shear beam body 22 is positioned between a rear abutment which, in this embodiment, is a clamp screw 30 and a front abutment which, in this embodiment, is a clamp screw 31. Rear clamp screw 30 is accessed through a hole (not shown) in backplate 20 and is threaded through the back plate portion 114 of clamp support block 23. Front clamp screw 31 is threaded through the front of the hood portion 112 of clamp support block 23. The front and rear clamp screws 30, 31 are adjustable during a setup procedure when the shear beam body 22 is in a neutral position with no lateral forces being applied to it. In this neutral position, the front and rear clamp screws 30, 31 are threaded inwardly towards the test tool 100 until they are in only very light contact with the shear beam body 22 and tool holder 200, respectively, causing little or no friction when the shear test 100 is moved in the Z-direction on the cantilever arms 21 relative to the clamp support block 23.

Figure 7:
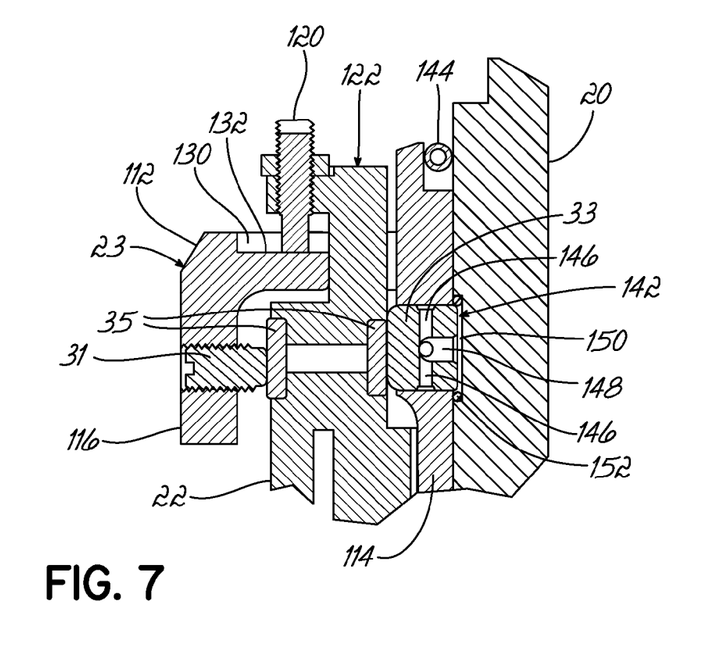
FIG. 7 is a partial cross-sectional view the pre-clamp piston 33 and other elements of the device.
Figure 8:
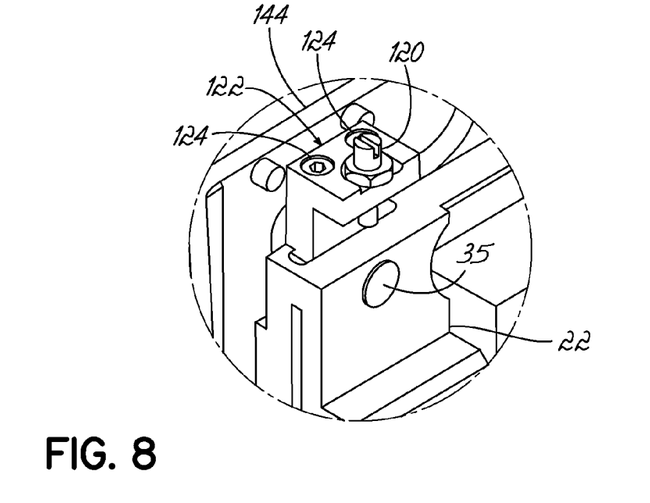
FIG. 8 is an enlarged perspective view of encircled area 8 showing a part of the shear testing device, with the clamp support block 23 removed to show the touchdown block 122 in more detail.

A clamp, or pre-clamp, piston 33 is positioned directly opposite the front clamp screw 31 as best shown in FIG. 7. Clamp piston 33 is located within a chamber, or hole, 142 in backplate 114 of clamp support block 23. Compressed air is supplied into chamber 142 through the compressed air supply line 144 shown in FIGS. 2-4 and 7-8. Once in the chamber 142, the compressed air enters the cross drilled holes 146, which have been drilled through piston 33. The air then enters bore 148 and exits the back of the piston 33 to pressurize the back chamber 150 which is formed in backplate 20. Back chamber 150 is sealed by O-ring 152, and consequently, the pressurized air trapped in chambers 142 and 150 forces piston 33 to the left in FIG. 7 to force it against shear beam body 22. When the pressurized air is removed, there is no appreciable force exerted by piston 33 against shear beam body 22, because piston 33 is freely movable within the hole 140 in backplate 14.

Thus, piston 33 is operable to move between a rest position where it does not exert an appreciable force against the shear beam body 22, and an actuated position, wherein it does exert an appreciable force against shear beam body 22 to clamp shear beam body 22, and thereby the test tool 100, between it and the front clamp screw 31. Clamp piston 33 when in its actuated position, holds the shear beam body 22, and shear tool 100, in a fixed position relative to the clamp support block 23 and back plate 20. This prevents any movement in the Z-direction, so that no further movement on the cantilever arms 21, or shear tool 100, is possible. There are other possible actuating mechanisms for the clamp piston. For example, it could be actuated by a solenoid or by a servo motor.

The clamp piston 33 is moved into the actuated position, fixing the position of the shear beam body 22, and tool 100, only when it has been determined by the detection of the optic beam by receiver 206 (as previously described) that the test head 10 of shear tool 100 has touched down on the substrate 300 under test. The clamp piston 33 can be referred to as a pre clamp mechanism because it provides an initial clamping mechanism to the shear tool 100 to prevent the shear tool 100 from moving as the ball deposit 302 is moved into engagement with the shear tool 100. However, as explained further below, the shear forces that act upon the shear tool 100 during a shear test enhance the clamping force on the shear tool 100.

Note that the shear tool 100 includes clamp pads 35 made from tungsten carbide or similar hard, tough material that are positioned opposite to the front and rear clamp screws 30, 31 and to the clamp piston 33. This ensures a good contact between the shear test tool 100 and the clamp screws 30, 31 and clamp piston 33, and ensures that there is minimal wear so that the system has good repeatability and an extended lifetime. Similarly, the front and rear clamp screws 30, 31 have contact surfaces made from hardened steel. The clamp piston 33 contact surface is made from brass or similar material to ensure smooth operation and is not hardened.

Once the clamp piston 33 has immobilised the shear test tool 100 relative to the backplate 20, the cartridge 11 is moved in the Z-direction away from the substrate a predetermined step off distance prior to performing a shear test. This procedure is standard in shear testing tools of this type, and is described in detail in WO 2005/114722.

During a shear test, an object under test exerts a shear force on the test tool head 10 of the shear tool 100 in a test direction, which is the direction of relative movement between the object and the test tool head 10 of the shear test tool 100. The test direction is indicated by arrow 36 in FIG. 3. The shear force exerted on the test tool head 10 of the shear tool 100 urges the test tool 100 against the front and rear clamp screws 30, 31. The load of the shear force is thereby transferred to the backplate 20 through the clamp screws 30, 31, rather than through the cantilever arms 21. The greater the shear force, the greater the load applied to the clamp screws 30, 31. This arrangement reduces the load experienced by the cantilever arms during a shear test. Thus, while the pre-clamp piston 33 initially clamps shear tool 100 in position, during a shear test, the shear forces themselves enhance the clamping force on the test tool 100.

In prior cartridge assemblies, the cantilever arms 21 had to withstand a large proportion of the shear forces experienced during a test. This leads to a requirement for more robust and hence more massive cantilever arms when carrying out shear tests at greater test loads. The more massive the cantilever arms, the greater the touchdown force that the shear test tool 100 exerted on a substrate 300 during the touchdown procedure prior to a shear test. However, with the clamp screw arrangement of the present invention, the cantilever arms 21 take minimal load, and consequently, they can be made relatively light weight.

Figure 9:
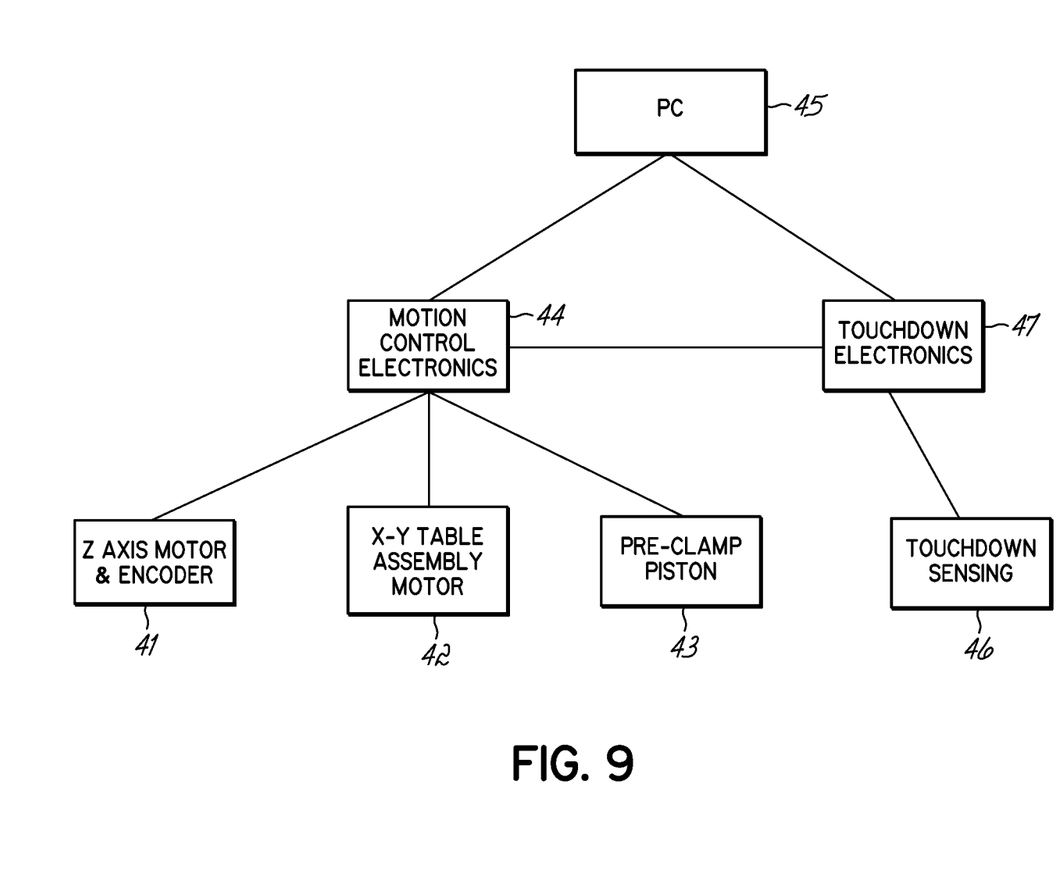
FIG. 9 is a schematic diagram showing the control elements of an apparatus in accordance with the present invention.

FIG. 9 is a schematic illustration of the control elements of a device in accordance with the present invention. The moving parts in the invention are: the axial drive mechanism, shown as a Z-axis motor and encoder 41; the motor 42 that drives the movement of the stage table 13 in the X-Y plane; and the clamp piston 43, which in the illustrated embodiment is a pneumatic piston. Each of these devices is controlled by dedicated motion control electronics 44, which is connected to a personal computer (PC) 45. The PC 45 also receives a signal from the optical sensor 202 to indicate the touchdown of the test tool 100 on a substrate 300. The optical sensor 202 is illustrated as box 46, and also has its own dedicated controller, referred to herein as touchdown electronics 47. There is a direct link between motion control electronics 44 and touchdown electronics 47. This allows swift signal response to ensure that the axial drive mechanism stops in the quickest possible time, to prevent over-travel and associated "heavy" touchdown.

Figure 10:
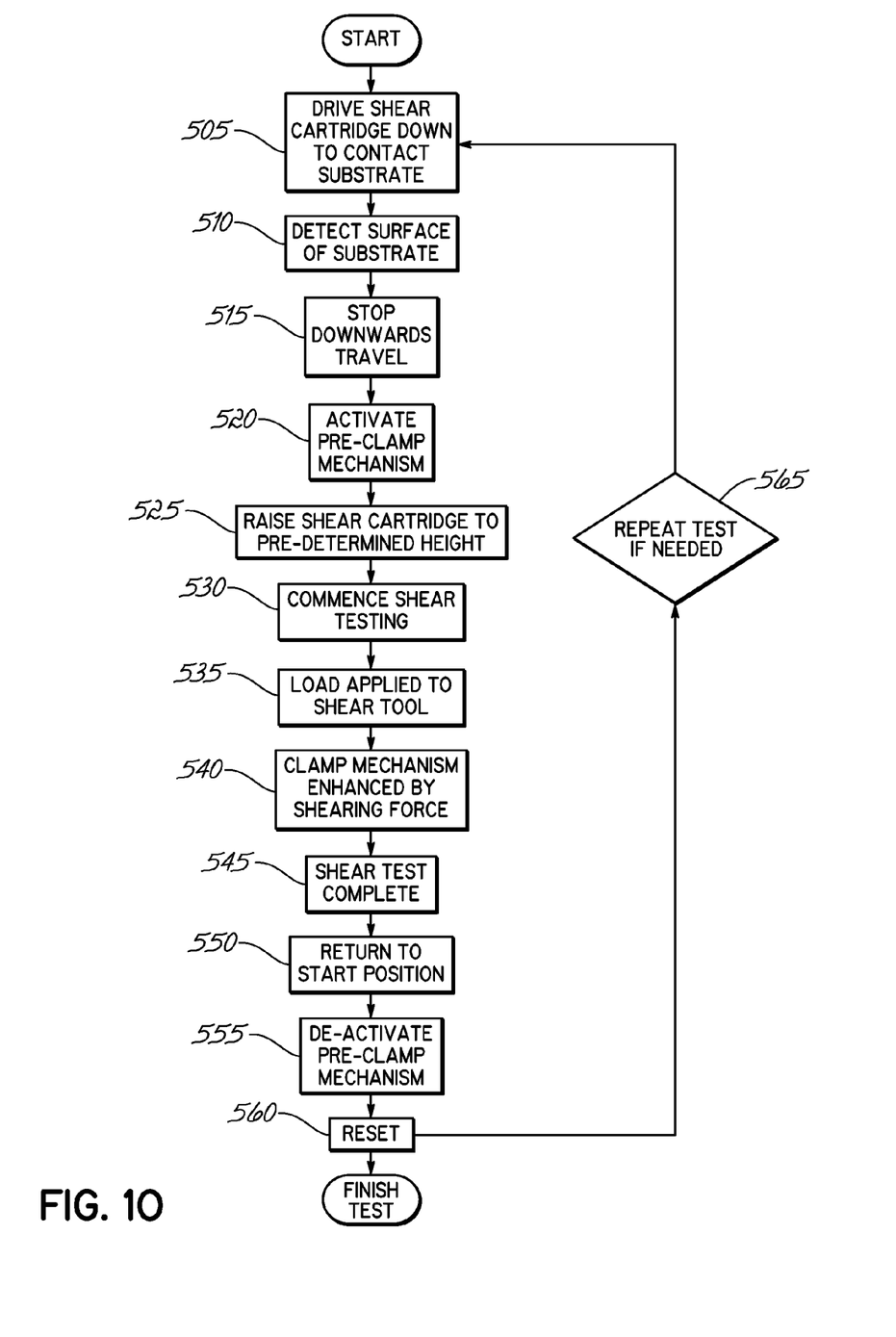
FIG. 10 is a flow diagram illustrating the method steps carried out in performing a shear test using an apparatus in accordance with the present invention.

FIG. 10 illustrates the steps taken in setting up and performing a shear test using an apparatus in accordance with the present invention. In a first step 505, the cartridge 11 and test tool 100 are moved down until test head 10 contacts the substrate 300. At step 510, the touchdown of the test head 10 on the surface of the substrate 300 is detected by detection of the optic beam by receiver 206, as previously described. When touchdown is detected, operation of the Z-axis motor that moves the shear cartridge 11 towards the substrate 300 is stopped at step 515. At step 520, compressed air is supplied to chambers 142 and 150 to move the pre-clamp piston 33 to its actuated position were in it forcibly contacts the shear beam body 22 to immobilise shear tool 100 relative to the back plate 20. At step 525, the cartridge is then moved away from the substrate to a predetermined step off distance in preparation for a shear test. At step 530, the shear test is commenced by moving the motorized table 13, and thereby the substrate 300 attached to it, so that a ball deposit 302 on the substrate 300 contacts the test tool head 10 to shear the ball deposit 302 off the substrate 300.

During the shear test, in step 535, a load, or force, is applied to the shear test head 10 as the test head 10 shears the ball deposit 302 off the substrate 300. This shear force is preferably picked up by strain gauges. As best shown in FIG. 5, in one preferred embodiment, four strain gauges 160a, 160b, 160c and 160d are bonded to tool holder 200. A cover 165 protects the strain gauges 160a-160d. Gauges 160a and 160b are on the front side of tool holder 200, facing the ball deposit 302 that will be sheared off substrate 300 during the shear test. Gauges 160c and 160d are on the opposite, or rear side, of tool holder 200.

Figure 11:
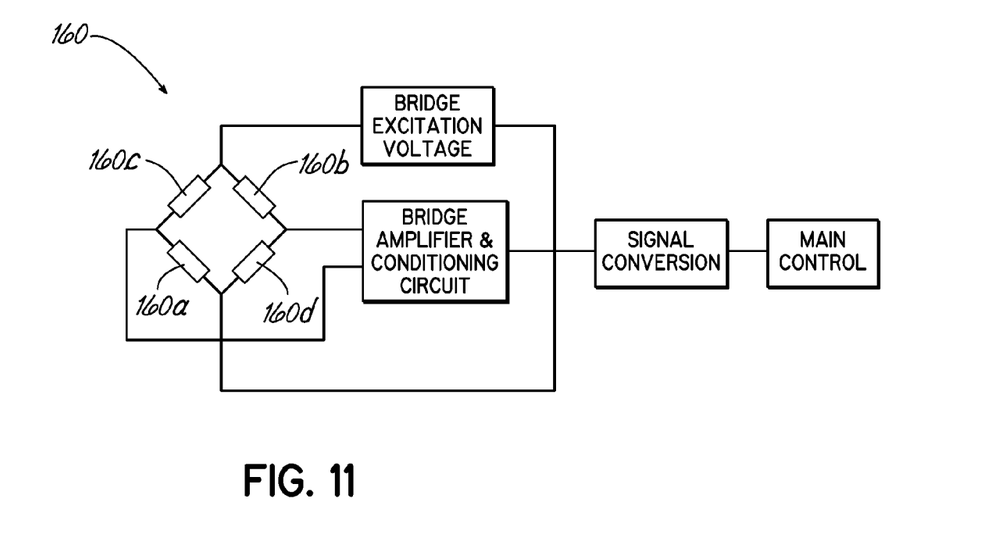
FIG. 11 is a schematic diagram of a circuit for detecting signals from the strain gauges 160a-160d.

The strain gauges 160a-160d are connected by wires (not shown) to an electric circuit, such as, for example, the full bridge circuit 160 shown schematically in FIG. 11. As is well known, such circuits convert electric signals caused by distortion of the strain gauges 160a-160d to force measurements, which indicate the force that was required to shear the ball deposit 302 off the substrate 300.

Alternatively, the shear force could be detected by a piezoelectric crystal mounted on the shear tool as described in the previously mentioned WO 2007/093799 A1. Using either force detection technology, as indicated at step 540, as the ball deposit 302 is driven against the shear tool 100, the front and rear clamp screws or abutments 30, 31 further enhance the clamping action on the shear tool 100, as described above.

At step 545 the shear test is completed and the shear test tool 100 is moved away from the substrate 300 and returned to a start position in step 550. At step 555 the clamp piston 33 is deactivated by removal of air pressure from chambers 142 and 150 so that the piston 33 can assume its rest position. This allows the shear test tool 100 to be moved in the Z-axis on the cantilever arms 21 by the drive mechanism. At step 560 the shear test can be repeated by performing the same method steps again, as shown in step 565.

Thus, referring to FIG. 2, a system in accordance with the present invention allows for a shear tool 100 to touchdown on a substrate under test with a relatively low, and adjustable, touchdown force. This low touchdown force is due to the relatively low mass of the cantilever arms 21 that is required for reasons described above. The system also allows the test tool 100 to be fixed relative to a mounting cartridge back plate 20 so that the vertical position of the test tool 100 can be accurately controlled. This is important for accurate and repeatable shear tests. As the shear load experienced by the shear test tool 100 is transferred to the cartridge backplate 20 via the clamping arrangement described, rather than via the cantilever arms 21, it is not necessary to have different cartridge assemblies for different load tests.

The invention claimed is:

1. A shear test device for testing the strength of attachment between a bond and an electronic substrate, comprising:
    an x-y table to which the substrate is adapted to be attached;
    a test tool;
    a drive mechanism that provides relative movement in a test direction between the table and the test tool;
    a baseplate, the test tool attached to the baseplate by a resilient connector allowing for movement of the test tool relative to the baseplate in an axial direction which is perpendicular to the test direction;
    at least one abutment that is rigidly fixed relative to the baseplate, the least one abutment being in contact with the test tool; and
    a clamping device rigidly fixed relative to the baseplate and moveable between a rest position wherein the clamping device is not forced against the test tool and an actuated position wherein the clamping device is forced against the test tool to maintain the test tool fixed in position relative to the baseplate in the axial direction, such that when the drive mechanism provides relative movement in the test direction between the table and the shear test tool to cause the shear test tool to shear the bond off the substrate during a shear test, the at least one abutment is positioned such that the force applied by the bond to the test tool causes the at least one abutment to provide an additional clamping force on the shear test tool.

2. A shear test device according to claim 1, wherein the clamping device comprises a single element that is forced against the test tool in the actuated position.

3. A shear test device according to claim 1, wherein when the clamping device is in the actuated position, the test tool is held between the clamping device and the at least one abutment.

4. A shear test device according to claim 1, wherein the at least one abutment comprises first and second abutments that are rigidly fixed in position relative to the baseplate.

5. A shear test device according to claim 4, wherein the first and second abutments are positioned in spaced apart relationship in the axial direction.

6. A shear test device according to claim 4, wherein the first and second abutments are located on opposite sides of the test tool.

7. A shear test device according to claim 4, wherein when the drive mechanism provides relative movement in the test direction between the table and the shear test tool to cause the shear test tool to shear the bond off the substrate during a shear test, the first and second abutments provide an additional clamping force on the shear test tool.

8. A shear test device according to claim 4, wherein the drive mechanism provides relative movement in a test direction along a test direction axis and wherein the position of the first and/or second abutments is adjustable along one or more axes that are parallel to the test direction axis.

9. A shear test device according to claim 1, further comprising a pneumatic mechanism configured to move the clamping device between the rest position and the actuated position.

10. A shear test device according to claim 9, wherein the clamping device is a pneumatically actuated piston.

11. A shear test device according to claim 1, further comprising a sensor configured to generate a signal when movement of the test tool relative to the baseplate in the axial direction is detected, and a controller connected to the sensor and to the clamping device, wherein the controller is configured to move the clamping device into the actuated position in response to the signal from the sensor.

12. A shear test device according to claim 1, wherein the test tool is received within a clamp support block that is fixed in position relative to the baseplate.

13. A shear test device according to claim 12, wherein the at least one abutment is attached to the clamp support block, and the clamping device is mounted in the clamp support block.

14. A shear test device according to claim 13, wherein the clamping device is a pneumatically actuated piston which is mounted in the clamp support block.

15. A shear test device according to claim 1, further comprising a touchdown block attached to the test tool, and a touchdown screw threaded through the touchdown block, and further comprising an optic sender and an optic receiver, and wherein an end of the touchdown screw can be positioned between the optic sender and the optic receiver, wherein the test tool is received within a clamp support block that is fixed in position relative to the baseplate, and wherein the optic sender and the optic receiver are mounted in the clamp support block on opposite sides of the touchdown screw.

* * * * *

UNITED STATES PATENT AND TRADEMARK OFFICE
CERTIFICATE OF CORRECTION

PATENT NO. : 8,607,641 B2  
APPLICATION NO. : 13/850460  
DATED : December 17, 2013  
INVENTOR(S) : David Lilley et al.

Page 1 of 1

It is certified that error appears in the above-identified patent and that said Letters Patent is hereby corrected as shown below:

In the Specifications

Column 1

Line 16, before "method" insert --a--.

Line 17, change "allows" to --allow--.

Line 18, change "maintains" to --maintain--.

Column 3

Line 7, after "attached" insert --to--.

Line 32, after "the" insert --at--.

Column 4

Line 19, after "with" insert --a--.

Line 30, after "view" insert --of--.

Column 6

Line 66, change "test" to --tool--.

Column 8

Line 52, after "position" delete "were in" and insert --wherein--.

In the Claims

Column 9

Claim 1, line 54, after "the" insert --at--.

Signed and Sealed this  
Fifteenth Day of April, 2014

Michelle K. Lee  
*Deputy Director of the United States Patent and Trademark Office*